United States Patent [19]
Seiler et al.

[11] Patent Number: 5,616,755
[45] Date of Patent: Apr. 1, 1997

[54] PROCESS FOR PREPARING LOW-CHLORIDE OR CHLORIDE-FREE AMINOFUNCTIONAL ORGANOSILANES

[75] Inventors: Claus-Dietrich Seiler; Hartwig Rauleder; Hans-Joachim Koetzsch, all of Rheinfelden; Hans-Guenther Srebny, Duelmen-Rorup, all of Germany

[73] Assignee: Huels Aktiengesellschaft, Marl, Germany

[21] Appl. No.: 527,873

[22] Filed: Sep. 14, 1995

[30] Foreign Application Priority Data

Sep. 14, 1994 [DE] Germany .......................... 44 32 638.6
Apr. 13, 1995 [DE] Germany .......................... 195 13 976.3

[51] Int. Cl.$^6$ ................................. C07F 7/08; C07F 7/10
[52] U.S. Cl. ........................ 556/413; 556/424; 556/466
[58] Field of Search ........................... 556/466, 413, 556/424

[56] References Cited

U.S. PATENT DOCUMENTS 5,210,254  5/1993  Ritscher et al. .................... 556/466
5,247,117  9/1993  Yamazaki et al. .................... 556/466

FOREIGN PATENT DOCUMENTS 0532872  3/1993  European Pat. Off. .
2521399  11/1976  Germany .

*Primary Examiner*—Paul F. Shaver
*Attorney, Agent, or Firm*—Oblon, Spivak, McClelland, Maier & Neustadt, P.C.

[57] ABSTRACT

The present invention relates to a process for preparing low-chloride or chloride-free aminofunctional organosilanes by reacting chlorofunctional organosilanes with organic amines or ammonia and separating off the organic hydrochlorides or ammonium chloride thus formed, wherein further amounts of organic hydrochlorides or ammonium chloride present are reacted by addition of metal alkoxides dissolved in alcohols and the metal chlorides formed are separated off, and also to aminofunctional organosilanes prepared thereby.

16 Claims, No Drawings

PROCESS FOR PREPARING LOW-CHLORIDE OR CHLORIDE-FREE AMINOFUNCTIONAL ORGANOSILANES

BACKGROUND OF THE INVENTION

1. Field of the Invention

The invention relates to a process for preparing low-chloride or chloride-free functional organosilanes by reacting chlorofunctional organosilanes with organic amines or ammonia and separating off the organic hydrochlorides or ammonium chloride thus formed, and also to aminofunctional organosilanes prepared according to the invention.

2. Discussion of the Background

Aminofunctional organosilanes are used conventionally in foundry technology as processing aids. They are also used as coupling agents for storage-stable resins or for glass fibre sizes.

Aminofunctional organosilanes are predominantly prepared by reaction of chlorofunctional organosilanes with organic amines of a wide variety of types or with ammonia. Aminofunctional organosilanes thus formed depend on the selected stoichiometric ratio of the amine component or the ammonia to the chlorofunctional organosilane. In the preparation of an aminofunctional organosilane compound, the procedure is generally to use at least 2 mol of amine or ammonia per mole of chloro-functional organosilane, so that, besides the formation of the aminofunctional organosilane, there is still sufficient amine component available to convert the chlorine replaced into the corresponding amine hydrochloride or ammonium chloride.

Various methods are used for separating off the amine hydrochloride or ammonium chloride formed in the synthesis from the target product, the aminofunctional organosilane.

For example, in the reaction of ammonia with 3-chloropropyltriethoxysilane, the amounts of ammonium chloride not dissolved in the aminopropyltriethoxysilane formed can be separated off from the product by simple filtration. Unfortunately, the remaining ammonium chloride dissolved in the aminopropyltriethoxysilane are disadvantageous for many applications. The ammonium chloride content of the product can be significantly lowered if the crude reaction product prior to filtration has added to it appropriate amounts of an inert medium, e.g. hydrocarbons such as petroleum ether, hexane or xylene, in which the aminosilane but not the ammonium chloride is soluble. Despite these measures, a residual amount of ammonium chloride remains in the filtrate. The usability of these aminosilane thus remains limited.

in other cases, in the preparation of aminofunctional, especially multiply aminofunctional, organosilanes, liquid two-phase systems are formed after the reaction is complete. Thus, for example, in the reaction of chloroorganofunctional silanes with ethylenediamine, the upper phase contains the product contaminated with excess amine and the dissolved hydrochloride thereof. After distillative removal of the amine component used, amine hydrochloride-containing doubly amino-functional organosilane remains which cannot be used in that form present, since its chloride content has an unfavorable influence on the properties of the product.

Reactions of chlorofunctional organosilanes with triply aminofunctional anilines frequently result neither in partial precipitation of the amine hydrochlorides formed in solid form nor in formation of phase systems. The removal of the amine hydrochlorides dissolved in the reaction system formed can be carried out only by appropriate dilution of the reaction product/amine hydrochloride/amine system with inert media in which the amine hydrochloride is not soluble. Even then, undesired residual amounts of amine hydrochloride remain in the product obtained after distillative removal of the inert medium and the amine component used in excess.

Despite the measures used in the preparation of aminofunctional organosilanes to separate off the organic hydrochlorides or the ammonium chloride formed, the products still contain undesired amounts of chlorides which limit the use opportunities of the products thus obtained or impair the desired effects.

SUMMARY OF THE INVENTION

It is therefore an object of the invention to develop a process for preparing low-chloride or chloride-free aminofunctional organosilanes.

It has now surprisingly been found that when metal alkoxides dissolved in alcohols are added to the aminofunctional organosilanes which are contaminated with an undesired amount of chloride, the metal chloride thus formed can be readily separated off and it is thus possible to obtain aminofunctional organosilanes whose residual chloride content can be made smaller than 1 ppm by weight.

The present invention accordingly provides a process for preparing low-chloride or chloride-free aminofunctional organosilanes by reacting chlorofunctional organosilanes with organic anilines or ammonia and separating off the organic hydrochlorides or ammonium chloride thus formed, which is characterized in that further amounts of organic hydrochlorides or ammonium chloride present are reacted by addition of metal alkoxides dissolved in alcohols and the metal chlorides formed are separated off.

The present invention further provides aminofunctional organosilanes which are further purified by reacting organic hydrochlorides or the ammonium chloride present therein with metal alkoxides and by separating off the metal chlorides thus formed.

DETAILED DESCRIPTION OF THE PREFERRED EMBODIMENTS

The aminofunctional organosilanes which can be prepared by the process of the invention can be described by the general formulae

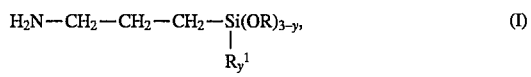

where

R is an alkyl radical having from 1 to 4 carbon atoms, $R^1$ is a methyl or phenyl radical, and y can be equal to 0 or 1 or 2;

where $R^1$ is an alkyl radical having from 1 to 3 carbon atoms, n can be equal to 2 or 3, p can be equal to 0 or 1, and a can be equal to 1 or 2 or 3;

$$[(R^1O)_3Si-(CH_2)_n]_{1-(NH-CH_2-CH_2)_p}-NH_2, \quad (IIb)$$

where

R$^1$ is an alkyl radical having from 1 to 3 carbon atoms,
n can be equal to 2 or 3, and
p can be equal to 2 or 3 or 4;

$$H_pN\begin{bmatrix}(CH_2)_nSi(OR)_{3-m}\\ R\quad R_m\end{bmatrix}_{2-p}, \quad (III)$$

where n can be equal to 1 or 2 or 3,
m can be equal to 0 or 1,
p can be equal to 0 or 1, and
R is an alkyl radical having from 1 to 3 carbon atoms; and $$RNH-(CH_2)_pNH_{1-m}-(CH_2)_n-Si(OR)_{3-m}, \quad (IV)$$
$$\qquad\qquad\qquad |\qquad\qquad\quad |$$
$$\qquad\qquad\qquad R_m\qquad\qquad\quad R_m$$

where n can be equal to 1 or 2 or 3,
m can be equal to 0 or 1,
p can be equal to 2 or 3, and
R is an alkyl radical having from 1 to 3 carbon atoms.

As starting materials for these compounds, chloroorganosilane compounds of the general formula $$Cl-(CH_2)_n-Si(OR)_{3-m}, \quad (V)$$
$$\qquad\qquad |$$
$$\qquad\qquad R_m$$

where n can be equal to 1 or 2 or 3,
m can be equal to 0 or 1 or 2, and
R is an alkyl radical having from 1 to 3 carbon atoms, can be reacted with amines of the general formulae $$H_nN(R)_{3-n}, \quad (VI)$$

where R is an alkyl radical having from 1 to 3 carbon atoms and n can be equal to 1 or 2 or 3;

$$NH_2-CH_2-CH_2-(NH-CH_2-CH_2-)_n-NH_2, \quad (VII)$$

where n can be equal to 0 or 1 or 2 or 3, and/or $$NH-CH_2-CH_2-NH, \quad (VIII)$$
$$|\qquad\qquad\qquad\quad |$$
$$R^1\qquad\qquad\qquad R^2$$

where R$^1$ and R$^2$ are each an alkyl radical having from 1 to 3 carbon atoms.

In this way, it is possible to obtain aminofunctional organosilanes as are listed below by way of example:

$$H_2N-CH_2-CH_2-CH_2-Si(OR)_3$$

$$H_2N-CH_2-CH_2-CH_2-Si(OR)_2$$
$$\qquad\qquad\qquad\qquad\qquad |$$
$$\qquad\qquad\qquad\qquad\qquad CH_3$$

$$HN(CH_3)-CH_2-CH_2-CH_2-Si(OR)_2$$
$$\qquad\qquad\qquad\qquad\qquad\qquad |$$
$$\qquad\qquad\qquad\qquad\qquad\qquad CH_3$$

$$H_2N-CH_2-CH_2-NH-CH_2-CH_2-CH_2-Si(OR)_2$$

$$H_2N-CH_2-CH_2-NH-CH_2-CH_2-NH-CH_2-CH_2-CH_2-Si(OR)_3,$$

where R is, for example, a CH$_3$ or C$_2$H$_5$ group.

After separating off the organic hydrochlorides or the ammonium chloride formed in the reaction from the aminofunctional organosilanes, these are treated with the metal alkoxides dissolved in alcohols to further lower the residual amount of chloride still present. Preferably, the metal alkoxides dissolved in alcohols are added in up to equivalent amounts based on the organic hydrochlorides or the ammonium chloride.

For the process of the invention, all known metal alkoxides of the elements of the Periodic Table which form salt-like metal halides can be used. Preferably, the metal alkoxide used is an alkoxide of the alkali metals and/or the alkaline earth metals. Particular preference is given to the alkoxides of sodium. The alkoxy groups of the metal alkoxides can be derived from primary, secondary and tertiary alcohols having from 1 to 6 carbon atoms, with particular preference being given to derivatives of primary alcohols having from 1 to 3 carbon atoms.

In a further preferred embodiment, in the alkaline component the alkoxide can be identical with the alkoxy groups located on the silicone atom of the aminofunctional organosilane. The solvent used for the metal alkoxide can also be the alcohol corresponding to the respective alkoxide, thus, for example, methanol, ethanol, n-propanol, isopropanol, tertiary butanol, tertiary amyl alcohol.

For the process of the invention, the alkoxides are preferably used in such amounts that there is no stoichiometric excess above the stoichiometrically required amount based on the chloride content in the substrate to be treated.

The lowering of the chloride content of an aminofunctional organosilane can advantageously be carried out by metering in only about 70–80% of the amount of alkoxide stoichiometrically required to completely eliminate the chloride content of the substrate, allowing it to react, again determining the residual content of organic hydrochloride or ammonium chloride after removal of the metal salts formed and again metering in, depending on the level of residual chloride remaining in the substrate, 70–80% of the stoichiometrically required amount of alkoxide. In this way, a controlled stepwise approach is made to the desired residual chloride content of the substrate, without exposing the product to the danger of discoloration as the result of an excess of alkoxide.

Furthermore, it has been found to be advantageous to carry out the reaction of the organic hydrochlorides or the ammonium chloride with the metal alkoxides while stirring at atmospheric pressure.

The reaction of the organic hydrochlorides or the ammonium chloride with the metal alkoxides can preferably be carried out at temperatures of from 0° C. to 100° C., particularly preferably at temperatures of from 20° C. to 80° C., very particularly preferably at from 20° C. to 50° C., It is advantageous to select the reaction temperature in such a way that the reaction time and the solubility of the metal salts formed in the substrate are minimized at the reaction temperature. The reaction can, for example, also be carried out under a protective gas atmosphere.

After completing the adjustment of the residual chloride content of the product in question to that desired, the metal salts formed are removed. The metal chlorides formed in the reaction can be separated off, for example, by filtration. The product can usually be used subsequently without further treatment. For certain applications, distillative removal of the alcohol introduced by the elimination of chloride may be required.

The metal salts formed in the process of the invention may sometimes be obtained in a form which is difficult to filter.

It is then possible to remove them by filtration with the aid of small amounts of filter aids, such as those based on diatomaceous earth (i.e., kieselguhr). However, the metal chloride formed in the reaction can also be particularly effectively removed by means of a separator. The removal of metal salts by means of a separator is particularly useful in the preparation of aminofunctional organosilanes on an industrial scale.

For the purposes of the present invention, chloride-free aminofunctional organosilanes mean those products whose chloride content is less than or equal to 1 ppm by weight. For the purposes of the present invention, low-chloride aminofunctional organosilanes mean those products whose chloride content is less than or equal to 30 ppm by weight. The process of the invention now allows such chloride-free or low-chloride aminofunctional organosilanes to be prepared.

In general, the process of the invention is carried out as follows:

A chlorofunctional organosilane is reacted with an organic amine or ammonia, preferably in a vessel having devices for heating, cooling and stirring, if desired in a pressure vessel. An aminofunctional organosilane and organic hydrochloride or ammonium chloride are thus formed. If the chloride-containing byproduct is obtained in a salt-like form, it is separated off from the reaction product, for example by filtration. It is also possible to add, beforehand, to the reaction or product mixture an inert liquid medium which is then, after separating off the salt, removed again from the reaction product together with excess amine or ammonia, for example by distillation. The pre-product thus obtained is analyzed for its chloride content by conventional methods. An equivalent amount of an alcoholic metal alkoxide solution corresponding to the chloride content determined is prepared and part of this is added while stirring to the pre-product at a previously set reaction temperature. After some time, a sample is taken, this is freed of the metal chloride formed and the chloride content now present is determined. A further part of the alcoholic metal alkoxide solution still available can subsequently be added to the aminofunctional organosilane in accordance with the desired residual chloride content. This procedure can also be carried out a plurality of times using smaller added amounts of metal alkoxide, taking into account the ratios of amounts with regard to the chloride. Finally, the metal chloride formed in the reaction of the undesired amounts of chloride with the metal alkoxide is removed from the target product. If small amounts of alcohol in the low-chloride or chloride free final product are a problem, these can be removed by distillation.

EXAMPLES

Having generally described this invention, a further understanding can be obtained by reference to certain specific examples which are provided herein for purposes of illustration only and are not intended to be limiting unless otherwise specified.

Example 1

In an autoclave, 2,415 g (10 mol) of 3-chloropropyltriethoxysilane were reacted with 17 kg (1,000 mol) of ammonia. After removing the excess ammonia, the reaction product was present in the autoclave in the form of a salt slurry consisting of ammonium chloride and predominantly 3-aminopropyltriethoxysilane. To reduce the amount of ammonium chloride dissolved in the organosilane, the contents of the autoclave were admixed while stirring at room temperature with 1,318 g of hexane. The salt was separated off by filtration. The filtrate obtained was freed of hexane by distillation under reduced pressure. The residue remaining had a weight of 1,989 g and its chloride content was detected as 550 ppm by weight. This corresponded to 1,094 mg of chloride.

The chloride-containing product was quantitatively transferred into a double-walled 3-liter five-neck flask fitted with stirrer, graduated dropping funnel, thermometer, water condenser and sampling ports. The contents of the flask were heated to 40° C. with intensive stirring. 10.472 g of a 20% strength ethanolic sodium ethoxide solution were weighed into the burette-shaped dropping funnel and diluted to a volume of 15 ml by addition of ethanol.

While maintaining the intense stirring in the flask, 11.25 ml of the sodium ethoxide solution in the dropping funnel were allowed to flow into the 3-liter flask. After a reaction time of about 15 minutes, a sample was taken from the flask and, after removal of the sodium chloride formed by filtration, the remaining chloride content of this sample was determined. It was found to be 145 ppm by weight. Of the 3.75 ml of sodium ethoxide solution remaining in the dropping funnel, a further 2.8 ml were metered into the contents of the flask. After a reaction time of 45 minutes had elapsed, another sample was taken from the flask and analyzed. The chloride content determined was 31 ppm by weight. Of the approximately 0.95 ml of sodium ethoxide solution remaining in the dropping funnel, a further 0.7 ml was added to the contents of the flask. After a reaction time of 1 hour had elapsed, a sample was again taken and analyzed. This showed a chloride content of 12 ppm by weight.

The contents were taken from the double-walled flask and freed of the sodium chloride formed, part of which was present in a colloidal state, by means of a separator. The clear filtrate of the aminofunctional organosilane was analyzed for its chloride content. A value of 8 ppm by weight was found.

The product can be used in this form, without further treatment, in foundry technology as coupling agent between sands and organic binders.

Example 2

In an autoclave, 1,985 g (10 mol) of 3-chloropropyltrimethoxysilane were reacted with 4,650 g (310 mol) of methylamine. After removal of the excess methylamine, the reaction product was present in the autoclave in the form of a salt slurry consisting of methylammonium chloride and predominantly 3-methylaminopropyltrimethoxysilane. The contents of the autoclave were admixed while stirring at room temperature with 1,318 g of hexane. The salt was separated off by filtration. The filtrate obtained was freed of hexane by distillation under reduced pressure. The remaining residue had a weight of 1,685 g and was found to have a chloride content of 1,675 ppm by weight. This corresponded to 2,822 mg of chloride.

This residue was quantitatively transferred into a double-walled 3-liter five-neck flask fitted with stirrer, graduated dropping funnel, thermometer, water condenser and sampling ports. The contents of the flask were heated to 45° C. with intensive stirring. 10.00 g of a 30% strength methanolic sodium methoxide solution were weighed into the burette-shaped dropping funnel. The sodium methoxide solution in the dropping funnel was allowed to flow into the double-walled flask over the course of ½ hour while maintaining the vigorous stirring. After the addition was complete, the mixture was allowed to react further for 30 minutes and subsequently a sample was taken from the contents of the flask and the chloride content of the sample was determined after separating off the precipitated sodium chloride. A chloride content of 490 ppm by weight was found in the filtrate, which corresponded to 826 mg of residual chloride. After rinsing the dropping funnel, an amount of 4.176 g of the 30% strength methanolic sodium methoxide solution was weighed into the same and subsequently diluted with methanol to a volume of 15 ml.

While maintaining the stirring, 12 ml of the sodium methoxide solution were allowed to flow from the dropping funnel into the suspension present over the course of 30 minutes. After a further reaction time of 15 minutes had elapsed, a sample was again taken from the contents of the flask and the residual chloride content was determined after separating off the precipitated sodium chloride. The chloride content was found to be 80 ppm by weight. After addition of a further 2 ml of sodium methoxide solution and after a further reaction time of 25 minutes had elapsed, an analyzed sample had a residual chloride content of 21 ppm by weight. A further addition of 0.7 ml of the sodium methoxide solution gave after a reaction time of 30 minutes, a chloride content of 2 ppm by weight in a sample. At this point, the addition of sodium methoxide solution was stopped and a part of the contents of the flask was filtered. The filtrate was turbid. The remaining part of the contents of the flask was passed through a separator. The filtrate obtained was clear.

Example 3

The procedure was as described in Example 1. However, the residual product obtained after distillative removal of the hexane under reduced pressure was subsequently worked up by fractional distillation under reduced pressure. This gave a distillate fraction having a weight of 1,702 g and a chloride content of 51 ppm by weight. This corresponded to 87 mg of chloride. The distillate was quantitatively transferred into a double-walled 3-liter five-neck flask and heated to 40° C. while stirring. 0.816 g of 20% strength ethanolic sodium ethoxide solution was weighed into the burette-shaped dropping funnel and was diluted to 10 m.1 by addition of ethanol.

7.5 ml of the sodium ethoxide solution were added to the distillate while stirring at atmospheric pressure. After reaction for one hour, a sample was taken and its chloride content was determined after removal of the precipitated sodium chloride. A value of 15 ppm by weight was found. Of the 2.5 ml of sodium ethoxide solution remaining in the dropping funnel, a further 1.8 ml were subsequently introduced into the contents of the flask. After a reaction time of one hour had elapsed, a sample was taken and the chloride content was determined. The value determined was 6 ppm by weight. The further addition of 0.6 ml of the ethanolic sodium ethoxide solution gave, after a reaction time of 1 hour, a chloride value <1 ppm by weight in the sample taken.

Example 4

In an autoclave, 1,985 g of 3-chloropropyltrimethoxysilane (10 mol) were reacted with 3,000 g of ethylenediamine at 90° C. The reaction product was present, after cooling, in two phases, with essentially all the product N-(2-aminoethyl)-3-aminopropyltrimethoxysilane present in the upper phase. separating off the upper phase gave 2,742 g of crude product. The chloride content was determined as 3,510 ppm by weight, corresponding to a total chloride content of 9,624 mg. The product separated off was quantitatively transferred into a double-walled 4-liter five-neck flask equipped with stirrer, graduated dropping funnel, thermometer, water condenser and sampling ports. The contents of the flask were heated to 50° C. while stirring. 45 g of 30% strength methanolic sodium methoxide solution were weighed into the dropping funnel over the course of 30 minutes, the amount of methoxide previously charged into the dropping funnel was added dropwise with intensive stirring. The sample taken was found to have a chloride content of 310 ppm by weight after removal of the precipitated sodium chloride. After rinsing the dropping funnel, 4.300 g of the 30% strength methanolic sodium methoxide solution were weighed into it and diluted to 15 ml with methanol. While maintaining the intensive stirring of the flask, 11 ml of the sodium methoxide solution present in the dropping funnel were allowed to flow into the 4-liter flask and, after a period of 15 minutes, a sample was taken. Determination of chloride in the filtrate of the sample gave a value of 71 ppm by weight. A further 2.7 ml of methoxide solution was added from the dropping funnel. After 25 minutes, a sample was taken. The determination of chloride in the filtrate gave a value of 27 ppm by weight. The further addition of 1.2 ml of methoxide solution resulted, after a reaction time of 20 minutes, in a residual chloride content of 7 ppm by weight in a sample.

The product present in the 4-liter flask, comprising aminofunctional organosilanes, ethylenediamine, sodium chloride and trace amounts of methanol, was transferred into a distillation apparatus and freed of the low boilers under reduced pressure with vigorous stirring. The distillation residue was, after cooling, passed through a separator and separated from the partially colloidal sodium chloride. A clear solution was obtained. The chloride content was found to be around 1 ppm by weight.

Example 5

5,150 g (50 mol) of diethylenetriamine were placed in a double-walled 12-liter four-neck flask equipped with stirrer, dropping funnel, thermometer and water condenser and were heated to 90° C. While stirring, 1 985 g (10 mol) of 3-chloropropyltrimethoxysilane were added from the dropping funnel over the course of 2 hours and were reacted with the initially charged amine. Subsequently, the reaction product was cooled to about 70° C. and admixed with 3.6 kg of xylene from the dropping funnel over the course of 1 hour. While stirring, the contents of the flask were cooled to room temperature and then stirred for a further period of about 5 hours. The contents of the flask, comprising aminoethylaminoethylaminopropyltrimethoxysilane, diethylenetriamine, xylene and diethylenetriamine hydrochloride, were filtered through a suction filter and the liquid phase was separated from the solids (diethylenetriamine hydrochloride). 9,205 g of filtrate were obtained. The filtrate was worked up by distillation under reduced pressure. in this procedure, xylene and diethylenetriamine were separated off and a distillation residue of 2,560 g was obtained, this consisting essentially of aminoethylaminoethylaminopropyltrimethoxysilane. The chloride content thereof was found to be 350 ppm by weight, corresponding to a total chloride amount of 896 mg. 4.543 g of 30% strength methanolic sodium methoxide solution were weighed into a graduated dropping funnel and made up to 10 ml with methanol. 7.5 ml of sodium methoxide solution from the dropping funnel were introduced into the distillation residue, which had been cooled to about 50° C., while stirring vigorously. After 25 minutes, a sample was taken from the flask and, after separating off the precipitated sodium chloride, the chloride content of the filtrate was found to be 71 ppm by weight. Of the 2.5 ml of sodium methoxide solution remaining in the dropping funnel, 1.7 ml were added to the contents of the flask. After 20 minutes, a sample was again taken and the chloride content in the filtrate was determined. The value was 15 ppm by weight. The further addition of 0.4 ml of sodium methoxide solution gave, after a further reaction time of 30 minutes had elapsed, a chloride content of 1–2 ppm by weight in a sample taken.

The precipitated sodium chloride, which was partially present in colloidal form, was separated off from the liquid phase by means of a separator. This gave a clear liquid in which a chloride content <1 ppm by weight was found.

Having now fully described the invention, it will be apparent to one of ordinary skill in the art that many changes and modifications can be made thereto without departing from the spirit or scope of the invention as set forth herein.

This application is based on German Applications P 44 32 638.6 filed Sep. 14, 1994 and P 195 13 796.3 filed Apr. 13, 1994; both incorporated herein by reference.

What is claimed as new and desired to be secured by Letters Patent of the United States is:

1. A process for preparing low-chloride or chloride-free aminofunctional organosilanes comprising:

reacting chlorofunctional organosilanes of the formula $$Cl-(CH_2)_n-Si(OR)_{3-m}$$
$$\phantom{Cl-(CH_2)_n-Si(O}R_m$$

where
n is 1 or 2 or 3,
m is 0 or 1 or 2, and
R each is an alkyl radical having from 1 to 3 carbon atoms, with organic amines of the formulas $$H_nN(R)_{3-n},$$

where R is an alkyl radical having from 1 to 3 carbon atoms $$NH_2-CH_2-CH_2-(NH-CH_2-CH_2-)_n-NH_2,$$

where n is 0 or 1 or 2 or 3 and/or $$NH-CH_2-CH_2-NH,$$
$$\phantom{NH-}|\phantom{CH_2-CH_2-}|$$
$$\phantom{NH-}R^1\phantom{H_2-CH_2-}R^2$$

where $R^1$ and $R^2$ are each an alkyl radical having from 1 to 3 carbon atoms to form alkylhydrochlorides, separating off said alkylhydrochlorides, further reacting any remaining alkylhydrochlorides with metal alkoxides dissolved in alcohols to form metal chlorides and separating off said metal chlorides, wherein said metal alkoxides dissolved in alcohols are added stepwise in up to stoichiometric equivalent amounts based on the alkyl hydrochlorides, the initial amount added being 70–80% of the stoichiometrically equivalent amount to completely eliminate the chloride content of the silanes, followed by removal of the metal salts formed, and one or more subsequent additions of the metal alkoxides dissolved in alcohols in amounts determined by the residual chloride content of the silanes.

2. The process according to claim 1, wherein said metal alkoxide used is an alkoxide of the alkali metals and/or the alkaline metals.

3. The process according to claim 1, wherein the reaction of said alkyl hydrochlorides with said metal alkoxides is carried out at temperatures of from 0° C. to 100° C.

4. The process according to claim 3, wherein the reaction of said alkyl hydrochlorides with said metal alkoxides is carried out at temperatures of from 20° C. to 80° C.

5. The process according to claim 4, wherein the reaction of said alkyl hydrochlorides with said metal alkoxides is carried out at temperatures of from 20° C. to 50° C.

6. The process according to claim 1, wherein the reaction of said alkly hydrochlorides with the metal alkoxides is carried out with stirring at atmospheric pressure.

7. The process according to claim 1, wherein said solvent used for the metal alkoxide is the alcohol corresponding to the respective alkoxide.

8. The process according to claim 1, wherein said metal chlorides formed in the reaction are separated off by filtration.

9. The process according to claim 1, wherein said-metal chloride formed in the reaction is separated off by means of a separator.

10. Low-chloride or chloride-free aminofunctional organosilanes produced by the process as defined by claim 1.

11. The aminofunctional organosilanes of claim 10, wherein the chloride content of said aminofunctional organosilanes is less than or equal to about 30 ppm.

12. The aminofunctional organosilanes of claim 11, wherein the chloride content of said aminofunctional organosilanes is less than or equal to about 10 ppm.

13. The aminofunctional organosilanes of claim 12, wherein the chloride content of said aminofunctional organosilanes is less than or equal to about 5 ppm.

14. The aminofunctional organosilanes of claim 13, wherein the chloride content of said aminofunctional organosilanes is less than or equal to about 1 ppm.

15. The process according to claim 1, wherein the alkoxy group of the metal alkoxides is of primary alcohol having from 1 to 3 carbon atoms.

16. The process according to claim 1, wherein the metal alkoxides dissolved in alcohols are an ethanolic solution of sodium ethoxide or a methanolic solution of sodium methoxide.

* * * * *